United States Patent [19]

Wiesmann

[11] Patent Number: 5,624,573
[45] Date of Patent: Apr. 29, 1997

[54] APPARATUS FOR THE DISINFECTION OF A FLOWING LIQUID MEDIUM AND A PLANT FOR THE TREATMENT OF CLARIFIED SEWAGE

[76] Inventor: Rudolf Wiesmann, Bogenackerstrasse 26, CH-8632 Tann, Switzerland

[21] Appl. No.: 443,067

[22] Filed: May 17, 1995

[30] Foreign Application Priority Data

May 17, 1994 [DE] Germany ............... 44 17 139.0

[51] Int. Cl.⁶ .................. C02F 1/32; A61L 9/20; F04F 10/02
[52] U.S. Cl. .............. 210/748; 210/198.1; 210/209; 210/258; 422/24; 422/186.3; 137/123; 137/142; 250/436
[58] Field of Search ................ 210/192, 198.1, 210/205, 209, 258, 748, 764; 422/24, 186.3; 137/123, 142; 250/432 R, 435, 436, 438; 138/39

[56] References Cited

U.S. PATENT DOCUMENTS

| | | | |
|---|---|---|---|
| 3,820,570 | 6/1974 | Holzhunter | 138/39 |
| 3,836,781 | 9/1974 | Ellison | 250/436 |
| 4,267,455 | 5/1981 | Keller | 210/192 |
| 4,367,410 | 1/1983 | Wood | 250/436 |
| 4,482,809 | 11/1984 | Maarschalkerweerd | 250/436 |
| 4,825,083 | 4/1989 | Latel et al. | 250/436 |
| 4,904,874 | 2/1990 | Ellner | 250/432 R |
| 5,019,256 | 5/1991 | Ifill et al. | 210/192 |
| 5,037,618 | 8/1991 | Hager | 250/436 |
| 5,151,174 | 9/1992 | Weismann | 210/192 |

Primary Examiner—Stanley S. Silverman
Assistant Examiner—Theodore M. Green
Attorney, Agent, or Firm—Tarolli, Sundheim, Covell, Tummino & Szabo

[57] ABSTRACT

An apparatus is disclosed for the disinfection of a liquid medium having a transmission of <75%/cm with the help of UV radiation. The apparatus comprises a plurality of UV radiators combined to a modular UV irradiation battery around which flows the liquid medium to be disinfected. Each UV radiator is oriented in parallel relationship to the flow direction of the liquid medium to be disinfected. The UV radiators are arranged in a matrix like array, particularly in a plurality of rows, each second row of said plurality of rows of UV radiators being offset with reference to the two adjacent rows by an amount corresponding essentially to half the center distance between two adjacent UV radiators located in the same row. The UV irradiation battery is enclosed by an essentially tube shaped housing, the inner contour of the housing essentially corresponding to the outer contour of the UV radiator battery.

22 Claims, 2 Drawing Sheets 5,624,573

APPARATUS FOR THE DISINFECTION OF A FLOWING LIQUID MEDIUM AND A PLANT FOR THE TREATMENT OF CLARIFIED SEWAGE

FIELD OF THE INVENTION

The present invention refers, in a first aspect, to an apparatus for the disinfection of a liquid medium, flowing in a predetermined direction, with the help of UV radiation, whereby this flowing liquid medium to be disinfected has, as far as the UV radiation is concerned, a transmission of <75%/cm. In a second aspect, the invention refers also to a plant for the disinfection of sewage incorporating an apparatus for the disinfection of a liquid medium, flowing in a predetermined direction, with the help of UV radiation, comprising a siphon means having an inlet and an outlet whereby the apparatus for the disinfection of sewage is located between the inlet and the outlet.

PRIOR ART

To disinfect flowing liquid media by means of UV radiation is known in the art for a long time. For this purpose, such plants are used worldwide in an unknown number which make use of such an UV irradiation apparatus or even a plurality of these apparatuses. For example, these apparatuses are used for the disinfection of clarified sewage in sewage clarification plants. In the prior art, these plants generally operate in a reliable manner, but have the disadvantage that the efficiency is quite low, particularly if the transmission of the sewage to be disinfected is below 75%/cm.

As far as the arrangement of the UV radiator member is concerned, in such apparatuses of the kind mentioned herein before, two generally different designs are used in the prior art:

1. The individual UV radiator members are arranged crosswise with respect to the direction of flow of the liquid medium to be treated.

2. The individual UV radiator members are arranged parallel with respect to the direction of flow of the liquid medium to be treated.

With the help of an example incorporating an apparatus used in a sewage clarification plant for an UV treatment of the clarified sewage, the general problems occurring with such UV irradiation designs shall be further explained. In order to disinfect the clarified sewage, the UV irradiation apparatus is usually inserted directly into the open sewage water channel. Because the water level of such sewage water channels varies with the amount of the accumulating water, the distance between the uppermost row of the active UV radiator members and the water level varies as well. However, such a situation should be avoided because, on the one hand, when the distance between the water level and the uppermost UV radiator member is too great, there is an insufficient disinfection effect in the upper level region of the water. On the other hand, if the above mentioned distance is too small, the UV radiator send their radiation unused to the atmosphere. Moreover, the danger exists that, the water level being low, the UV radiator members and the protective envelope tubes, respectively, are not sufficiently cooled with the result that the UV irradiation apparatus cannot operate with an optimal operating temperature. In order to provide for an optimal water level, it would be necessary to use very expensive control installations.

A further general problem in this connection is that in such installations of the kind referred to the channels in which the UV irradiation apparatus is inserted often shows great tolerances as far is its dimensions are concerned. The result is that the distance between the outermost UV radiator members and the walls and the bottom, respectively, of the channel varies along the longitudinal extension of the channel, leading to different and known disadvantages to be shortly discussed herein after:

If the distance between UV radiator member and channel wall varies, the cross section through which the water flows varies as well with the result that different flow conditions exist. For example, undesired eddies can occur. Moreover, the sewage flowing through the apparatus is not subjected to a continuous and even dose of UV radiation. This can lead to an insufficient disinfection. In order to take into account the tolerances of such channels, a comparatively great distance must be accepted between the outermost UV radiator members and the channel walls. However, this results in the fact that the sewage flowing through the apparatus in these regions is disinfected to a lower degree. Moreover, experience has shown that the efficiency of such plants is quite low.

U.S. Pat. No. 4,367,410 discloses a method and an apparatus for purifying secondary waste water effluent by UV radiation. A plurality of UV lamps are concentrically mounted within support jackets arranged in parallel and extending transversely across the fluid flow path of the waste water to be treated. Adjacent jackets are spaced less than about one half inch apart so that none of the waste water is more than about one quarter inch away from a Jacket as it flows past the lamps. The lamps are received in a housing which is provided, on both sides, with a rectangular opening. Through this openings, the waste water flows into the apparatus to flow around the UV lamps.

A disadvantage of this apparatus is that not the entire channel cross sectional area is available for the irradiation of the waste water. Moreover, by the design of this apparatus and the arrangement of the individual UV lamps, a quite high pressure drop can be observed which is highly undesirable due to the comparatively low slope of waste water channels.

U.S. Pat. No. 4,825,083 discloses an UV water treatment plant in which individual UV lamp units are loosely and retractably located within frames located in a water treatment channel. Individual frame supporting arrays of parallel lamp units may be removed from the channel, and the lamp units may be individually disengaged from the frame and disassembled for lamp replacement. The level of water in the channel is controlled according to the rate of flow, and the lamp units are selectively energized according to whether they are immersed so as to match the irradiation provided to the rate and cross section of the flow. A disadvantage of this design is that an expensive control mechanism must be present for the control of the energizing of the lamp units and/or for keeping the water level constant. Moreover, no constant and equal flow conditions can be achieved with such a design in which the individual lamps are oriented cross wisely to the direction of flow of the waste water to be treated.

OBJECTS OF THE INVENTION

Thus, it is an object of the invention to provide an apparatus for the disinfection of a liquid medium which has a distinctively higher efficiency than the apparatus known in the art and which is, simultaneously, of a very simply and inexpensive design.

SUMMARY OF THE INVENTION

In order to meet these and other goals, the present invention provides an apparatus for the disinfection of a liquid medium, flowing in a predetermined direction, with the help of UV radiation. The flowing liquid medium to be disinfected has, as far as the UV radiation is concerned within the object of the invention, a transmission of <75%/cm.

The apparatus of the invention comprises a plurality of individual UV radiator means, each being enclosed by a protective envelope tube which is essentially permeable for UV radiation.

All these UV radiator means are combined to a modular UV irradiation battery around which flows the liquid medium to be disinfected.

Each UV radiator member is oriented in parallel relationship to the flow direction of the liquid medium to be disinfected, such that the liquid medium to be disinfected flows parallel to the longitudinal extension of each of the UV radiator members.

The UV radiator members are arranged, as seen in a cross sectional plane running perpendicular to the predetermined direction of flow of the liquid medium to be disinfected, in a matrix like array. Moreover, the UV radiator members, as seen in one direction of the above mentioned cross sectional plane, are arranged in a plurality of rows, each second row of said plurality of rows of UV radiator members being offset with reference to the two adjacent rows by an amount corresponding essentially to half the center distance between two adjacent UV radiator members located in the same row.

The modular UV irradiation battery is radially enclosed by an essentially tube shaped housing. The inner contour of the housing essentially corresponds to the outer contour of the plurality of UV radiator members given by the particular arrangement of the UV radiator members and envelope tube members, respectively. The wall of the housing has a certain distance with reference to the outermost located UV radiator members.

BRIEF DESCRIPTION OF THE DRAWINGS

In the following, the apparatus according to the invention will be further described, with reference to the accompanying drawings, in which an embodiment of the essential parts of the disinfection plant according to the invention is shown. Particularly, in the drawings.

DETAILED DESCRIPTION OF A PREFERRED EMBODIMENT

Figure 1:
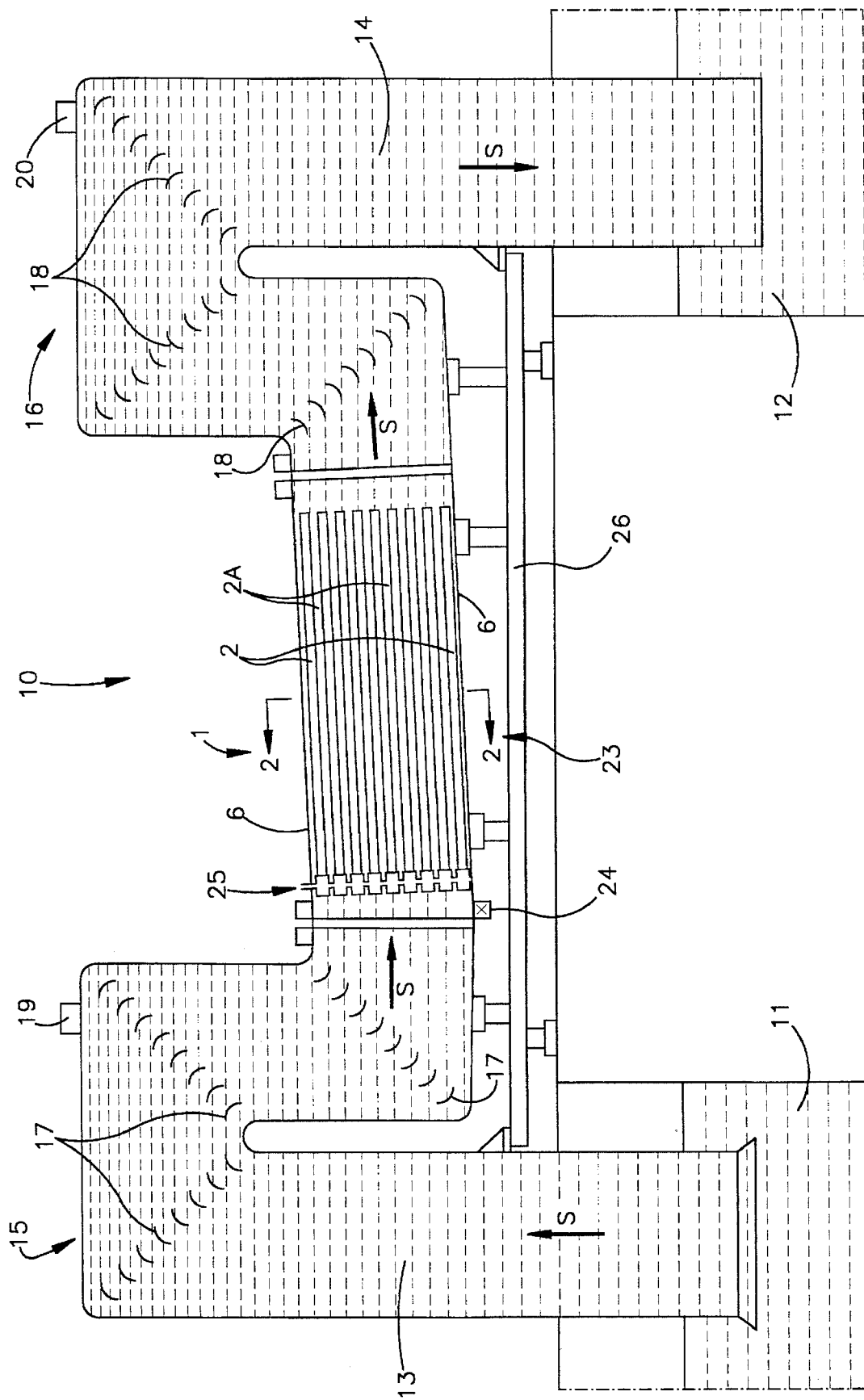
FIG. 1 shows a schematical longitudinal sectional view of a plant incorporating an apparatus for the disinfection of fluids.

In FIG. 1, there is schematically shown, in a longitudinal sectional view, a plant incorporating an apparatus for the disinfection of fluids. For example, such a design can be used for the disinfection of clarified sewage which is withdrawn from a sewage clarification plant.

An open discharge conduit, through which the clarified sewage is withdrawn from a sewage clarification plant, comprises a head-water conduit and a low-water conduit separated from the former. In the present example, only a section 11 of the headwater conduit and a section 12 of the low-water conduit are shown in the drawings. The two conduit sections 11 and 12, respectively, run parallel to each other and have different water levels. The two sections 11, 12 are connected to each other by an overground tube array which is generally designed as a siphon member and designated with reference numeral 10. The siphon member 10 is provided with an inlet tube member 13 dipping into the headwater section 11 and a outlet tube member 14 leading to and dipping into the section 12 of the low-water conduit. As seen in the direction of flow of the sewage, indicated by the reference sign s in the drawings, through the siphon member 10, the latter one is provided with a first overflow bend member 15 located after the inlet tube member 13 and with a second overflow bend member 16 located in front of the outlet tube member 14. The two overflow bend members 15 and 16 are interconnected by means of an intermediate tube member 23 which is gently sloping upwards in the direction of flow s of the sewage. Incorporated in the above mentioned intermediate tube member 23 is the apparatus 1 for the disinfection of fluid.

The apparatus I for the disinfection of fluid comprises a plurality of individual UV radiator members 2 which are integrated into an UV irradiation battery. The longitudinal extension of each UV radiator member 2 runs parallel to the direction of flow s of the sewage. The UV radiator members 2 are radially enclosed by a generally tube-shaped housing member 6.

The two overflow bend members 15 and 16 are connected to the just mentioned housing member 6 and are provided with means for positively influencing the flow of the sewage, in the present example with guiding paddle members 17 and 18. The guiding paddle members 17 and 18 are located in the interior of the two overflow bend members 15 and 16, particularly, as seen in a longitudinal sectional view according to FIG. 1., along diagonal lines in the bends of the two overflow bend members 15 and 16, respectively. These guiding paddle members 17 and 18 have the effect that the sewage is moving in the kind of a plug flow, not only in the region in front of the inlet tube member 13, but also in the region behind the outlet tube member 14.

At the deepest point of the intermediate member 23 which interconnects the two overflow bend members 15, 16 of the siphon 10, there is provided a drain valve member 24 by means of which the siphon 10 as well as the entire assembly can be drained. At the highest point of each of the two overflow bend members 15, 16, there is provided a valve member 19 and 20, respectively. By connecting these two valve members 19 and 20 to a sub atmospheric pressure source, the siphon 10 can be put into operation. On the other hand, if the two valve members 19 and 20 are opened, the siphon 10 is put out of operation because air is sucked in through the open valves 19 and 20 during operation of the siphon 10 with the result that its normal operation is interrupted. The operation of the siphon 10 having been interrupted by opening the valve members 19 and 20, the entire assembly can be drained by opening the valve member 24.

From time to time, it is necessary to stop the operation of the entire apparatus 1 in order to clean it. Once the entire assembly having been drained, the apparatus can be filled with a cleaning fluid for a periodical servicing which is necessary after a certain period of operation. Moreover, if the entire assembly is drained, the apparatus 1 can be disassembled easily, for instance in order to replace some of the radiator members 2, or to replace the entire radiator battery.

To provide the radiator battery with the required electrical energy, there is schematically shown in FIG. 1 a power supply connection leading to the outside of the apparatus 1.

The principal mode of operation of such a siphon assembly 10 is well known in the art; thus, it is not necessary to explain it here in detail. For this reason, the following explanations are limited to the essential.

The sewage flowing through the inlet tube member 13 into the siphon member 10 is led to the input side of the apparatus 1 via the overflow bend member 15 provided at the inlet side of the assembly. In the interior of the overflow bend member 15, the sewage flowing there trough is guided by the guiding paddle members 17 in such a way that a plug flow is realized at the input of the radiator battery or radiation apparatus 1. In other words, the sewage shows an essentially constant flowing speed over the entire cross sectional area.

Thereafter, the sewage flows along the individual UV radiator members 2 through the apparatus 1 and is disinfected under the UV radiation present in the interior of the apparatus 1. In this way, the germ index of the sewage can be reduced by three logarithmic steps which generally is required in an efficient sewage disinfection plant.

When the disinfected sewage has passed the UV radiator assembly 1, if flows through the second overflow bend member 16 and is guided by means of the guiding paddle members 18 provided therein to guarantee a continuous flow of the sewage in order to avoid a negative repercussion of the flow behavior in the interior of the apparatus 1. Finally, the thus disinfected sewage is led via the outlet member 14 into the low-water conduit 12.

Thanks to the facts that, on the one hand, the UV radiator battery is radially enclosed by a housing 6 and, on the other hand, the entire apparatus 1 for the UV irradiation of the sewage is integrated in a siphon assembly 10 as has been explained herein before, it is ensured that the UV irradiation apparatus 1 is always completely filled with the fluid to be treated, in the present ample with sewage, over its entire cross sectional area; this means that always all UV radiator members 2 are enclosed by sewage and therefore can operate most effectively.

The entire siphon assembly 10 as well as the UV irradiation apparatus are supported by a supporting frame 26 on the ground.

Figure 2:
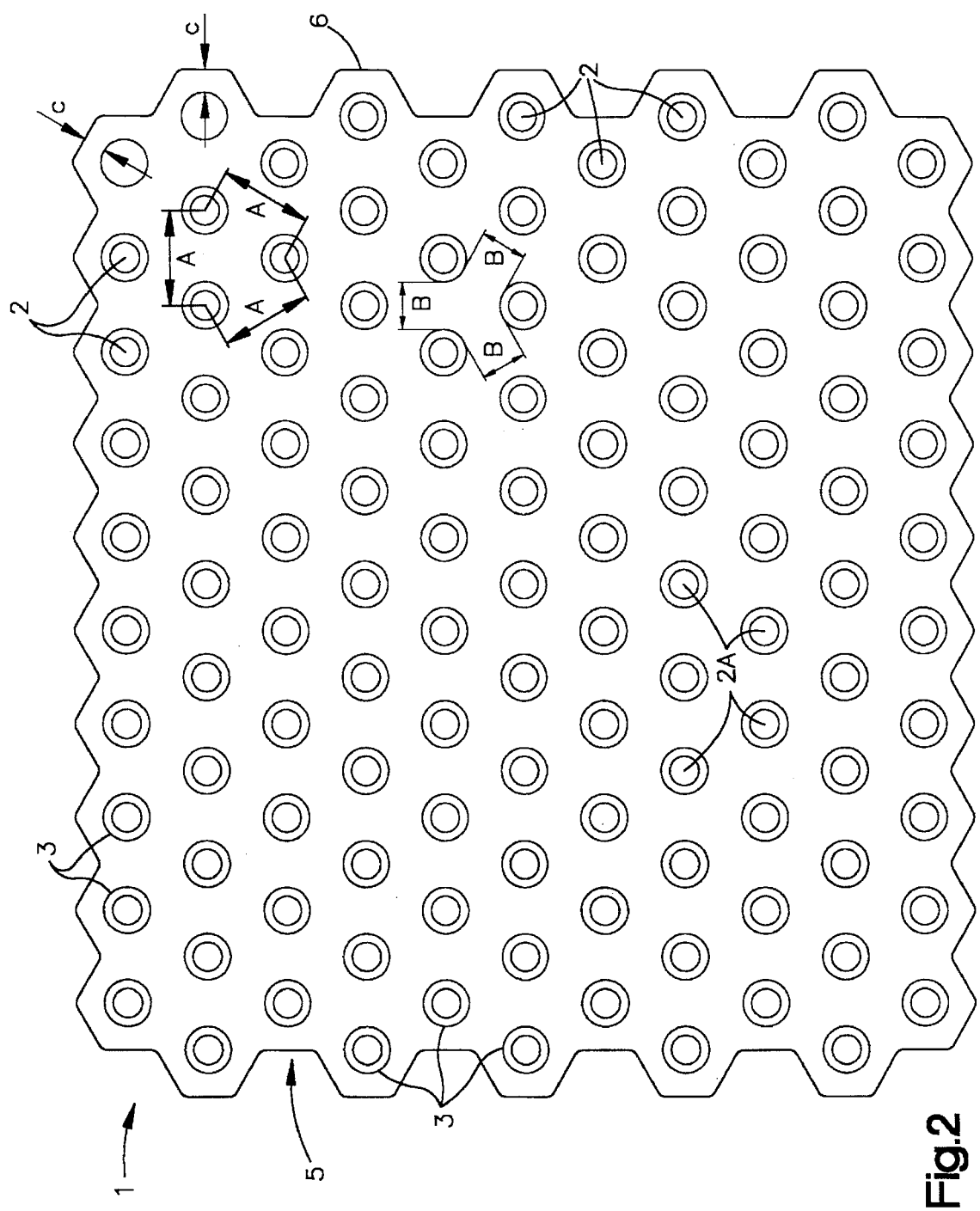
FIG. 2 a cross sectional view of an UV radiation emitting apparatus for the treatment of the fluid, taken along the line A—A in FIG. 1.

In FIG. 2, there is shown a cross sectional view of the UV irradiation apparatus 1, taken along the line A—A indicated in FIG. 1. In this FIG. 2, only the essential parts of the UV irradiation apparatus are schematically shown and all electrical connector members and all fastening means for the UV radiators 2, 2A have been omitted for clarity's sake.

The explanation which wall follow herein after again refer to the example in which the UV irradiation apparatus is used in a water clarification plant, particularly for the disinfection of sewage.

Referring now to FIG. 2, the apparatus for UV-irradiation of the sewage and, thereby, for the disinfection of the sewage, comprises, as already mentioned, a plurality of individual UV radiator members 2, 2A which together are integrated into an UV irradiation battery 5. The UV irradiation Battery 5 is enclosed by a housing 6, the shape of which being of general tubular design and closely following the outer shape of the irradiation battery.

The wave length of the individual radiator members 2, 2A used for the disinfection of sewage preferably lies in the region of between 250 and 270 nm. In this manner, i.e. by the irradiation battery 5 and the housing 6, a radiation chamber is formed in which the disinfection of the sewage takes place. As can be seen from the illustration in FIG. 2, the radiator members 2, 2A are arranged in a matrix like design, as seen in the cross sectional view taken perpendicularly to the direction of flow of the sewage to be disinfected. As can be Been in FIG. 2, the individual radiator members 2, 2A are arranged in rows in the one direction, in the present example in the horizontal direction, whereby each two rows of radiator members 2, 2A are offset to each other by a distance amounting essentially to half the distance A between two adjacent radiator members 2, 2A lying in the same row. In the cross sectional view of FIG. 2, this results in a triangle configuration of the radiator members 2, 2A. Moreover, the arrangement, particularly the distance between two adjacent rows is such that the thus resulting triangle has equal lengths of its sides.

The housing 6 radially enclosing this radiator member assembly 5 is designed such that its inner contour corresponds with the outer contour of the radiator member battery 5, i.e. closely follows the outer shape of the outermost located radiator members 2. In order to protect the individual radiator members 2, 2A from environmental influences and in order to keep their operating temperature as constant as possible, all radiator members 2, 2A are enclosed by a envelope tube member 3 which is transparent for UV radiation.

The distance B between two adjacent envelope tubes members 3 preferably amounts to between 20 and 50 mm; this results in a center distance A between two adjacent radiator members 2, 2A of between 40 and 50 mm because the envelope tubes 3 usually have a diameter of between 20 to 35 mm.

Experiments have shown that in the case of sewage coming from a clarification plant and having a transmission of 40 to 70% $cm^{-1}$, a distance between adjacent envelope tubes 3 of 30 mm is ideal and results in the best efficiency of disinfection.

In order to better illustrate the distance C between the outermost envelope tubes 3 and the wall of the outer housing 6, the two radiator members 2 located in the interior of the envelope tubes 3 in the top right corner of the illustration of FIG. 2 are not shown. The above mentioned distance C corresponds approximately to half the distance B between two adjacent envelope tubes 3, i.e. to approximately 15 mm.

Because the sewage circulating between the outermost radiator members 2 and the wall of the housing 6 is subjected to the UV radiation emitted by the radiator members 2 only from one side, the intensity of the UV radiation and, thereby, the disinfection effect on the sewage flowing through this region is lower than in the case of sewage flowing centrally through the UV irradiation battery 1. However, due to the design of the UV irradiation battery 1 and, in particular, of the housing 6, as mentioned herein above, i.e. less distance between wall of the housing 6 and the outermost radiator members 2 than between adjacent radiator members 2A, it is ensured that sewage flowing through the region between the outermost radiator members 2 and the wall of the housing has a lower flow speed than sewage flowing throng the central region of the UV irradiation apparatus 1 where the radiator members 2A are located. Thus, the dwell or residence time of the sewage flowing through the apparatus 1 in the region of the housing walls is increased, with the result that radiation dose affecting the sewage, which is composed by the irradiation intensity and the irradiation time, is increased. In the present example, the radiation dose is essentially the same either in the case of the afore mentioned edge regions as in the central regions of the UV irradiation battery. Thus, the entire sewage flowing through the apparatus 1, with reference of the cross sectional area, is equally treated by the UV radiation emitted by the UV irradiation battery. Also the pressure drop in the sewage flow, as measured over the cross sectional area of the apparatus 1, is essentially equal for the entire amount of sewage flowing through the apparatus 1.

In the following, the most important characteristics of the apparatus according to the invention are summarized:

The apparatus for the disinfection of fluids, particularly of sewage, comprises a plurality of UV radiator members which are combined to form a UV irradiation battery and which are arranged, with reference to the longitudinal extension, in parallel to the direction of flow of the fluid to be treated.

The individual radiator members are arranged, as seen in a cross sectional view through the irradiation battery, in a matrix like design, with a plurality of rows of radiator members, each row of radiator members being offset with respect to the adjacent row of radiator members by an amount corresponding approximately to half center distance between two adjacent radiator members.

The UV irradiation battery is radially enclosed by a housing whose inner wall contour which essentially corresponds to the outer contour given by the location of the individual UV radiator members and the envelope tubes surrounding them, respectively.

The distance between adjacent envelope tubes amount to between 20 and 50 mm.

The distance between the inner side of the housing and the in each case closest radiator member essentially corresponds to half the distance between two adjacent envelope tubes.

Particularly the last mentioned measure ensures that the flow speed of the fluid to be treated which flows through the apparatus in the region between the outermost radiator members and the housing wall is lower than of the fluid flowing through the apparatus in the central region thereof. In this way, the radiation dose authoritative for the disinfection of the fluid and, in this example, the sewage, is essentially equal over the entire cross sectional area of the disinfection apparatus.

What is claimed is:

1. An apparatus for the disinfection of a liquid medium flowing in a predetermined direction and having a transmission of <75%/cm, said apparatus comprising:

a plurality of individual UV radiator means, each of said UV radiator means being enclosed by a protective envelope essentially permeable to UV radiation;

said plurality of UV radiator means being integrated in a modular UV irradiation battery means through which flows the liquid medium to be disinfected;

each UV radiator means of said plurality of UV radiator means being oriented in a parallel relationship to said predetermined flow direction of said liquid medium to be disinfected, such that the liquid medium to be disinfected flows parallel to the longitudinal extension of each of said UV radiator means;

said plurality of UV radiator means being arranged, as viewed in a cross sectional plane running perpendicular to said predetermined direction of flow of said liquid medium to be disinfected, in a plurality of uniformly spaced lateral rows, each of said plurality of rows comprising a plurality of uniformly spaced UV radiator means, said plurality of UV radiator means comprising a first group of said UV radiator means radially enclosing a second group of said UV radiator means, said first group of UV radiator means comprising at least one of said plurality of UV radiator means from each of said plurality of rows;

said modular UV irradiation battery means and said plurality of said UV radiator means being radially enclosed by an essentially tube-shaped housing means, said housing means being defined by a wall means which is essentially uniformly spaced from each of said UV radiator means in said first group of UV radiator means a distance of about one-half of the distance between the center of two adjacent UV radiator means located in the same row.

2. An apparatus as defined in claim 1 wherein each of said plurality of rows comprises a first UV radiator means, a last UV radiator means, and a plurality of intermediate UV radiator means disposed between said first and last UV radiator means, said plurality of rows comprising an outermost first row, an outermost last row, and a plurality of intermediate rows disposed between said first and last rows, each second row of said plurality of rows of UV radiator means being offset with reference to the two adjacent rows of UV radiator means by an amount corresponding to about one-half of the distance between the center of two adjacent UV radiator means located in the same row.

3. An apparatus as defined in claim 2 wherein said first group of said UV radiator means comprises each of said UV radiator means in said first and last rows of said plurality of rows of UV radiator means and said first and last UV radiator means in each of said intermediate row of UV radiator means, said second group comprising each of said intermediate UV radiator means in every intermediate row of UV radiator means.

4. An apparatus as defined in claim 3 wherein the distance between the center of two adjacent of said protective envelope means enclosing said UV radiator means is between about 20 and 50 mm.

5. An apparatus as defined in claim 4 wherein the distance between the center of two adjacent UV radiator means is between about 40 and 80 mm.

6. An apparatus as defined in claim 5 wherein said housing wall means has means for reducing the flow speed of the liquid medium to be disinfected flowing between said UV radiator means in said first group and said housing wall means relative to the flow speed of the liquid medium to be disinfected flowing between two adjacent UV radiator means.

7. An apparatus as defined in claim 6 wherein said housing wall means has means for providing that the radiation dose which is authoritative for the disinfection of the liquid medium is essentially constant over the cross-sectional area of said apparatus.

8. An apparatus as defined in claim 7 wherein the distance between the inner side of said housing wall means and said protective envelope means of the closest of said plurality of UV radiator means is about one-half of the distance between the center of two adjacent protective envelope means.

9. A plant for the disinfection of sewage, comprising a disinfection apparatus as defined in claim 1.

10. A plant for the disinfection of sewage as defined in claim 9, further comprising a siphon means having an inlet means and an outlet means, said apparatus for the disinfection of sewage being located between said inlet and said outlet means.

11. A plant for the disinfection of sewage according to claim 10 further comprising, as seen in the flow direction of the sewage to be disinfected, a first overflow bend means located behind said inlet means and a second overflow bend means located in front of said outlet means, said apparatus for the disinfection of sewage being located between said first overflow bend means and said second overflow bend means.

12. A plant for the disinfection of sewage as defined in claim 11, wherein said first overflow bend means is provided with flow guiding means in order to provide for a plug flow in the sewage to be disinfected in a region before the sewage enters said disinfection apparatus.

13. A plant for the disinfection of sewage as defined in claim 12, wherein said second overflow bend means is provided with flow guiding means in order to provide for a plug flow in the sewage to be disinfected in a region after the sewage has left said disinfection apparatus.

14. A plant for the disinfection of sewage as defined in claim 13 wherein said flow guiding means comprises a plurality of guiding paddle members located along diagonally extending straight lines in the bends of said first overflow bend means and said second overflow bend means, respectively.

15. A plant for the disinfection of sewage as defined in claim 14 wherein said siphon means comprises an intermediate portion in which said disinfection apparatus is located, said intermediate portion interconnecting said first overflow bend means and said second overflow bend means and having an intermediate portion inlet and an intermediate portion outlet, said intermediate portion inlet being located at a lower level than said intermediate portion outlet.

16. A plant for the disinfection of sewage as defined in claim 15 wherein said intermediate portion is provided with a drain valve member located at its lowest level point.

17. A plant for the disinfection of sewage as defined in claim 16 wherein each of said first overflow bend means and said second overflow bend means is provided with a vent valve means located at the highest points thereof, as seen in the flow direction of the sewage to be disinfected.

18. A process for the disinfection of water comprising flowing the water through the plant as defined in claim 9.

19. A process for the sterilization of clarified sewage in a sewage clarification installation comprising flowing the sewage through the as defined in claim 9.

20. A process for the disinfection of water comprising flowing the water through the apparatus as defined in claim 1.

21. A process for the sterilization of clarified sewage in a sewage clarification plant comprising flowing the sewage through the apparatus as defined in claim 1.

22. An apparatus for the disinfection of a liquid medium flowing in a predetermined direction and having a transmission of <75%/cm, said apparatus comprising:

a plurality of individual UV radiator means, each of said UV radiator means being enclosed by a protective envelope essentially permeable to UV radiation;

said plurality of UV radiator means being integrated in a modular UV irradiation battery means through which flows the liquid medium to be disinfected;

each UV radiator means of said plurality of UV radiator means being oriented in a parallel relationship to said predetermined flow direction of said liquid medium to be disinfected, such that the liquid medium to be disinfected flows parallel to the longitudinal extension of each of said UV radiator means;

said plurality of UV radiator means being arranged, as viewed in a cross sectional plane running perpendicular to said predetermined direction of flow of said liquid medium to be disinfected, in a plurality of lateral rows, each of said plurality of rows comprising a plurality of uniformly spaced UV radiator means, each of said plurality of rows further comprising a first UV radiator means, a last UV radiator means, and a plurality of intermediate UV radiator means disposed between said first and last UV radiator means, said plurality of rows comprising an outermost first row, an outermost last row, and a plurality of intermediate rows disposed between said first and last rows, each second row of said plurality of rows of UV radiator means being offset with reference to the two adjacent rows of UV radiator means by an amount corresponding to about one-half of the distance between the center of two adjacent UV radiator means located in the same row, said plurality of rows being arranged in such a way that said plurality of UV radiator means comprises a first group of said UV radiator means radially enclosing a second group of said UV radiator means, said first group of said UV radiator means comprising each of said UV radiator means in said first and last rows of said plurality of rows of UV radiator means and said first and last UV radiator means in every intermediate row of UV radiator means, said second group comprising each of said intermediate UV radiator means in every intermediate row of UV radiator means;

said modular UV irradiation battery means and said plurality of said UV radiator means being radially enclosed by an essentially tube-shaped housing means, said housing means being defined by a wall means, said wall means being essentially uniformly spaced from each of said UV radiator means in said first group of UV radiator means by such a distance that the volume of liquid medium flowing between said first group of UV radiation means and said housing wall means is about one-half of the volume flowing between the center of two adjacent UV radiator means located in the same row.

* * * * *